United States Patent [19]
Kim

[11] Patent Number: 5,894,067
[45] Date of Patent: *Apr. 13, 1999

[54] COMPOSITION FOR GENERATING FAR INFRARED RAYS

[76] Inventor: Young Shin Kim, 4955 Bramhope La., Elliott City, Md. 21043

[*] Notice: This patent is subject to a terminal disclaimer.

[21] Appl. No.: 08/827,100

[22] Filed: Mar. 17, 1997

Related U.S. Application Data

[60] Continuation of application No. 08/517,414, Aug. 21, 1995, abandoned, which is a division of application No. 08/203,608, Feb. 28, 1994, Pat. No. 5,451,199, which is a continuation of application No. 07/959,425, Oct. 13, 1992, abandoned.

[51] Int. Cl.$^6$ .............................. C04B 35/95; C09K 11/08
[52] U.S. Cl. .................... 501/128; 501/125; 252/301.36; 252/301.4 R; 252/301.4 F; 428/917
[58] Field of Search .................... 501/19, 73, 128, 501/125; 252/301.4 R, 301.36, 301.4 F; 428/917

[56] References Cited

U.S. PATENT DOCUMENTS

| | | | |
|---|---|---|---|
| 4,162,672 | 7/1979 | Yazaki | 600/15 |
| 5,451,199 | 9/1995 | Kim et al. | 600/9 |

FOREIGN PATENT DOCUMENTS

| | | | |
|---|---|---|---|
| 0214368 | 3/1987 | European Pat. Off. | 600/9 |

*Primary Examiner*—Karl Group
*Attorney, Agent, or Firm*—Birch, Stewart, Kolasch & Birch, LLP

[57] ABSTRACT

A portable device for carrying with the human body includes a far infrared ray generating composition plate, a magnetic radiating unit, an electronic circuit unit, and a mercury battery disposed on the far infrared ray generating composition plate for self-radiating bioenergy so as to eliminate and reduce human fatigue and stress. The composition of the plate including 24–27 parts by weight of $SiO_2$, 53–55 parts by weight of $Al_2O_3$, 13–15 parts by weight of CaO, 1–4 parts by weight of MnO, 1–3 parts by weight of $TiO_2$, and 1–2 parts by weight of Ag, the sum of the $SiO_2$, $Al_2O_3$, CaO, MnO, $TiO_2$, and Ag equalling 100 parts by weight.

11 Claims, 1 Drawing Sheet

COMPOSITION FOR GENERATING FAR INFRARED RAYS

This application is a continuation application under 37 C.F.R. §1.53 of Ser. No. 08/517,414 filed on Aug. 21, 1995, now abandoned, which is a divisional application under 37 C.F.R. §1.60 of Ser. No. 08/203,608 filed Feb. 28, 1994, now U.S. Pat. No. 5,451,199, which is a continuation application under 37 C.F.R. §1.62 of Ser. No. 07/959,425 filed Oct. 13, 1992, now abandoned, the entire contents of which are hereby incorporated by reference.

BACKGROUND OF THE INVENTION

1. Field of the Invention

The present invention relates to a novel portable therapeutic device having a far infrared ray (extreme infrared ray) generating composition and more particularly, to a device comprising a magnetic radiating unit, an electronic circuit unit, and a mercury battery unit disposed on a far infrared ray generating composition plate for self-radiating bioenergy to the user so as to eliminate or reduce fatigue and stress of the person who carries the device.

2. Description of the Related Art

There are many types of devices which may be used to reduce and eliminate fatigue and stress in humans, which are well known in the art. For example, a permanent magnet has been used for accelerating the circulation of human blood in order to reduce or eliminate human fatigue and/or stress. However, these devices cannot fully generate far infrared rays and an electronic circuit and a mercury battery together with a specific inorganic composition are not utilized, and thus these devices fall short of expectations.

SUMMARY OF THE INVENTION

Accordingly, it is an object of the present invention to provide a novel portable therapeutic device which eliminates the above problems encountered in a conventional magnetic device.

Another object of the present invention is to provide a handy device comprising a far infrared ray generating composition plate, which supports a magnetic radiating unit, an electronic circuit unit, and a mercury battery unit for transferring self-radiating bioenergy to the wearer to eliminate and/or reduce fatigue and stress in the human being who carries it.

A further object of the present invention is to provide a far infrared ray generating plate made of a composition comprising, by weight 24–27% of $SiO_2$, 53–55% of $Al_2O_3$, 13–15% of CaO, 2–4% of MnO, 1–3% of $TiO_2$, and 1–2% of Ag as an alloy or embedded in a resinous carrier material.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a portable device which is carried by the human body, which comprises a far infrared ray generating composition plate, and a magnetic radiating unit, an electronic circuit unit, and a mercury battery disposed on the far infrared ray generating composition plate for self-radiating bioenergy so as to eliminate and reduce human fatigue and stress

BRIEF DESCRIPTION OF THE DRAWINGS

The present invention will become more fully understood from the detailed description given hereinbelow and the accompanying drawings which are given by way of illustration only, and thus, are not limitative of the present inventions and wherein.

PREFERRED EMBODIMENTS OF THE INVENTION

Figure 1:
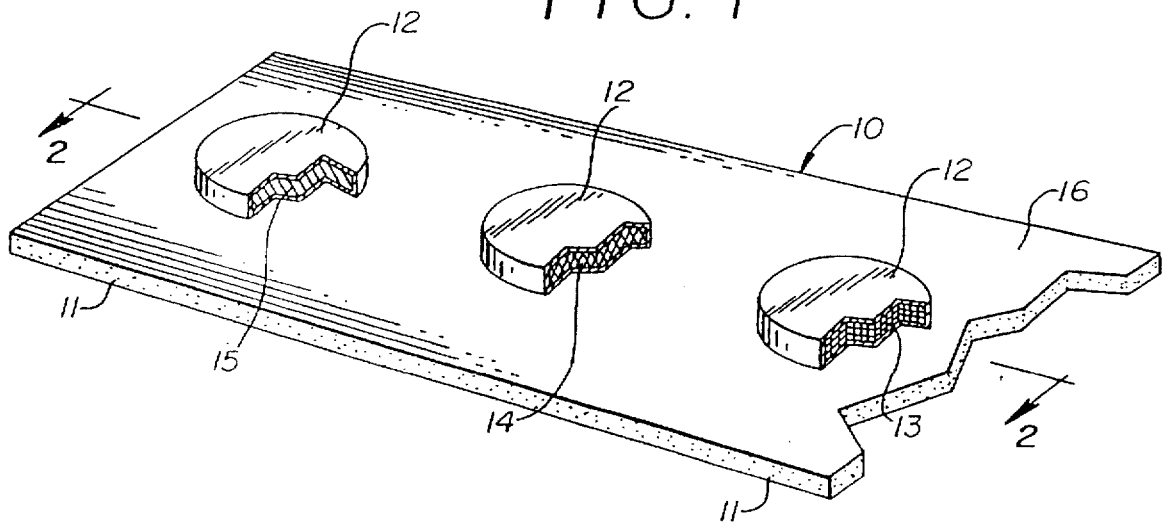
FIG. 1 is a perspective view of the portable device containing a cut-away portion in order to illustrate the construction of the device according to the present invention.
Figure 2:
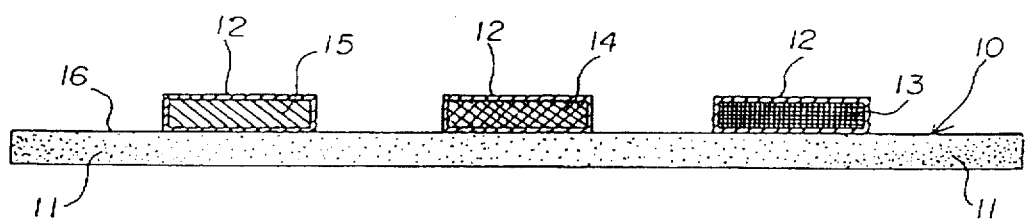
FIG. 2 is a sectional view of FIG. 1, taken along line 2—2.

Referring now in detail to the drawings for the purpose of illustrating preferred embodiments of the present invention, the portable device 10 as shown in FIGS. 1 and 2, comprises a far infrared ray generating composition plate 11, a magnetic radiating unit 13, an electronic circuit unit 14, and a mercury battery unit 15 disposed on the far infrared ray generating composition plate 11. The magnetic radiating, electronic circuit, and mercury battery units 13, 14, and 15 are covered with a gold layer 12.

The portable device 10 is a bioenergy radiator which self-radiates from the radiating material which makes up the plate 11. Thus, the device automatically radiates bioenergy and magnetic waves which are equivalent to the magnetic waves generated at the same time by the earth. The radiation device does not cause excessive far infrared rays to emanate from the system, nor from the magnetic force of natural origin.

The far infrared rays are produced from the motion energy of the composition of the plate itself which is composed of the self-radiating material and they are also produced by simple agitation (motion energy)

Magnetic force waves are produced and radiated through the electronic circuit 14, and have about the same wave length as that received by the earth at the North Pole area. Thus, in the same time period it is possible to radiate a magnetic force which is double the norm.

In general, the main function of the radiating system of a conventional far infrared ray device is to generate perspiration which releases waste material from the living body, depending on its temperature. As the temperature increases, the far infrared ray device can be used to dry even the inside of those objects that necessitate such techniques. The conventional device can also be used to preserve agricultural products;

In normal living, there is frequently no opportunity for many people to take part in healthy exercise procedures, and even if such exercise is possible, it frequently makes them fatigued and thus adds to their stress. By utilizing the device of the present invention close to one's body, he or she can obtain the good results of exercise, free from fatigue, and other destructive symptoms associated with normal exercise which prevent him or her from performing his or her daily activities with a high degree of precision.

It is believed that the living body can be replenished with energy by carrying the device of the present invention which radiates far infrared rays and magnetic force waves together with natural waves in connection with the energy cycle the living body and rhythm of the living body of a healthy human body.

The device of the present invention provides radiation which is helpful in recovering from stress, and thus helpful in maintaining the health and coordination of the human body.

Human beings, animals, and plants have bodies composed of water and protein which are the basic ingredients of life. The highly polymerized living body is made of protein, cells, nucleic acid, enzymes, etc. Protecting the high polymers of the living body and holding the key for effectively balancing the body structure is a water screen. To break down this water screen means the eventual death of the living body.

Water molecules consist of one oxygen atom and two hydrogen atoms, wherein the oxygen atom is disposed in between the two hydrogen atoms. These water molecules are polar in nature which means that the hydrogen atoms and the oxygen atoms are charged. Since hydrogen has a plus charge and oxygen has a negative charge, the direction of motion is changed. Electric pressure is produced due to the difference between these electrical charges. As the water molecules radiate due to their electromagnetic force, friction is produced. The heat of oscillation increases the heat energy to radiate the hydrogen atom, and the hydrogen atoms create deformation vibration, oscillated together, and rotary vibration, etc. due to the excited state created in the human body at the molecular level. This effect is achieved by carrying or wearing the absorptive radiating device of the present invention. Thus, it is possible to generate heat in the living body tissue, and accelerate molecular movement due to the ionization of the existing condition which helps stimulate the tissue of the living body and balance the activation of body function.

Most of the living body contains combined water molecules, and the radiating panel of living body energy which disposes of all sorts of body reactions which cause mental stress is obtained. The portable device 10 contains a far infrared radiating material which supplies body energy due to an external source, for accelerating the internal body functions.

As shown in FIG. 1, the far infrared ray generating composition plate 11 is composed on a weight basis of 24–26% $SiO_2$, 53–55% $Al_2O_3$, 13–15% CaO, 1–4% MnO, 1–3% $TiO_2$, and 1–2% Ag, all of which have a particle size of about 5–10 microns as an alloy, and the substantial balance being a plastic material, which is present in an amount of about 20% by weight. The composition plate 11 preferably contains, by weight, 26% of $SiO_2$, 54% of $Al_2O_3$, 14% of CaO, 3% of MnO, 1.7% of $TiO_2$, and 1.3% of Ag. This composition is heated at a temperature of about 1,100° to form a fused mixture. The fused mixture is placed into a thin aluminum layer case 16.

The magnetic radiating unit 13, covered with the thin gold layer 12, is attached to one end portion of the composition plate 10. The mercury battery unit 15, covered with the thin gold layer 12, is attached to the other end portion of the composition plate 10. The electronic circuit unit 14 is attached to the composition plate 10 and is disposed between the magnetic radiating unit 13 and the mercury battery unit 15. The units 13, 14, and 15 all have a columnar configuration.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A composition comprising 24–27 parts by weight of $SiO_2$, 53–55 parts by weight of $Al_2O_3$, 13–15 parts by weight of CaO, 1–4 parts by weight of MnO, 1–3 parts by weight of $TiO_2$, and 1–2 parts by weight of Ag; the sum of the $SiO_2$, $Al_2O_3$, CaO, MnO, $TiO_2$, and Ag equalling 100 parts by weight.

2. The composition according to claim 1, wherein said $SiO_2$, $Al_2O_3$, CaO, MnO, $TiO_2$, and Ag are each in the form of a powder having a particle size of about 5–10 microns.

3. The composition according to claim 1, wherein said $SiO_2$, $Al_2O_3$, CaO, MnO, $TiO_2$, and Ag are each in the form of a powder having a particle size of about 5–10 microns and are each embedded in a resinous carrier material.

4. The composition according to claim 3, wherein said resinous carrier material comprises a plastic material of approximately 20 parts by weight; the sum the of the $SiO_2$, $Al_2O_3$, CaO, MnO, $TiO_2$, Ag, and plastic material equaling 120 parts by weight.

5. The composition according to claim 1, wherein said $SiO_2$, $Al_2O_3$, CaO, MnO, $TiO_2$, and Ag are each in the form of a powder and are each embedded in a resinous carrier material.

6. The composition according to claim 5, wherein said resinous carrier material comprises a plastic material of approximately 20 parts by weight; the sum the of the $SiO_2$, $Al_2O_3$, CaO, MnO, $TiO_2$, Ag, and plastic material equaling 120 parts by weight.

7. The composition according to claim 1, wherein said composition comprises 26 parts by weight of $SiO_2$, 54 parts by weight of $Al_2O_3$, 14 parts by weight of CaO, 3 parts by weight of MnO, 1.7 parts by weight of $TiO_2$, and 1.3 parts by weight of Ag.

8. The composition according to claim 7, wherein the composition is in the form of a plate that was produced by fusing an admixture of said $SiO_2$, $Al_2O_3$, CaO, MnO, $TiO_2$, and Ag.

9. The composition according to claim 8, wherein said fusing is carried out by heating at a temperature of about 1100° C.

10. The composition according to claim 1, wherein the composition is in the form of a plate that was produced by fusing an admixture of said $SiO_2$, $Al_2O_3$, CaO, MnO, $TiO_2$, and Ag.

11. The composition according to claim 10, wherein said fusing is carried out by heating at a temperature of about 1100° C.

* * * * *